United States Patent
Kim et al.

(10) Patent No.: US 10,699,164 B2
(45) Date of Patent: Jun. 30, 2020

(54) TRAINING TEMPLATE CONSTRUCTION APPARATUS FOR FACIAL EXPRESSION RECOGNITION AND METHOD THEREOF

(71) Applicants: The Industry & Academic Cooperation in Chungnam National University (IAC), Daejeon (KR); Taehyun Kim, Yongin-si (KR)

(72) Inventors: Taehyun Kim, Yongin-si (KR); Soo Rim Noh, Daejeon (KR)

(73) Assignees: THE INDUSTRY & ACADEMIC COOPERATION IN CHUNGNAM NATIONAL UNIVERSITY (IAC), Daejeon (KR); Taehyun Kim, Yongin-si (KR)

(*) Notice: Subject to any disclaimer, the term of this patent is extended or adjusted under 35 U.S.C. 154(b) by 60 days.

(21) Appl. No.: 16/164,970

(22) Filed: Oct. 19, 2018

(65) Prior Publication Data
US 2020/0104637 A1    Apr. 2, 2020

(30) Foreign Application Priority Data
Sep. 27, 2018   (KR) ........................ 10-2018-0115261

(51) Int. Cl.
  *G06K 9/62*     (2006.01)
  *G06K 9/00*     (2006.01)
  *G06K 9/68*     (2006.01)
(52) U.S. Cl.
  CPC ....... *G06K 9/6256* (2013.01); *G06K 9/00248* (2013.01); *G06K 9/00281* (2013.01); *G06K 9/00617* (2013.01); *G06K 9/685* (2013.01)
(58) Field of Classification Search
  CPC .. G06K 9/6256; G06K 9/00281; G06K 9/685; G06K 9/00248; G06K 9/00617
  See application file for complete search history.

(56) References Cited

U.S. PATENT DOCUMENTS

| 9,363,569 B1* | 6/2016 | van Hoff ............ H04N 21/2668 |
| 2013/0054622 A1* | 2/2013 | Karmarkar ............ G06F 16/951 |
| | | 707/749 |

(Continued)

FOREIGN PATENT DOCUMENTS

| KR | 10-2009-0001324 | 1/2009 |
| KR | 10-2010-0066866 | 6/2010 |

(Continued)

OTHER PUBLICATIONS

Rizwan Ahmed Khan et al., "Exploring human visual system: study to aid the development of automatic facial expression recognition framework", Conference Paper, Jul. 2012.

(Continued)

*Primary Examiner* — Wesley J Tucker
(74) *Attorney, Agent, or Firm* — Lex IP Meister, PLLC

(57) ABSTRACT

A training template construction apparatus includes a gaze fixation point receiving unit for receiving gaze fixation points of a user that looks a facial picture that expresses random emotion, from an eye tracking apparatus that is operatively associated with the gaze fixation point receiving unit, a gaze pattern extraction unit for extracting a gaze pattern and gaze pattern information via machine-learning of the gaze fixation points received from the gaze fixation point receiving unit, a heat map deduction unit for deducing a heat map using the gaze pattern and the gaze pattern information that are extracted by the gaze pattern extraction unit, a difference heat map deduction unit for deducing a difference value between the heat map deduced from the heat map deduction unit and a heat map of a reference group based on pre-stored facial pictures that express the same emotion and for deducing a difference heat map to which the difference value is applied, and a controller for analyzing the gaze pattern and the difference heat map to generate a training (Continued)

template of a sequence, a time, and a path for user gaze treatment.

15 Claims, 15 Drawing Sheets
(11 of 15 Drawing Sheet(s) Filed in Color)

(56) References Cited

U.S. PATENT DOCUMENTS

| | | | | |
|---|---|---|---|---|
| 2015/0135309 | A1* | 5/2015 | Karmarkar | G06F 16/532 726/19 |
| 2016/0091967 | A1* | 3/2016 | Prokofieva | G06F 3/013 345/156 |
| 2017/0115742 | A1* | 4/2017 | Xing | G06F 3/015 |
| 2018/0314321 | A1* | 11/2018 | Primus | A63F 13/50 |
| 2019/0019581 | A1* | 1/2019 | Vaughan | A61B 5/7267 |
| 2019/0043610 | A1* | 2/2019 | Vaughan | A61B 5/4088 |
| 2019/0196576 | A1* | 6/2019 | Saarinen | G06F 3/013 |
| 2019/0328830 | A1* | 10/2019 | Chang | A61K 31/485 |
| 2019/0362133 | A1* | 11/2019 | Margolin | G06K 9/00302 |

FOREIGN PATENT DOCUMENTS

| | | |
|---|---|---|
| KR | 10-2014-0046652 | 4/2014 |
| KR | 10-2017-0107229 | 9/2017 |

OTHER PUBLICATIONS

Soo Rim Noh et al., "Development of Facial Emotion Recognition Enhancement Training Algorithm in Schizophrenia Patients through Facial Emotion Recognition Pattern Analysis", 2017 Annual Meeting Korean Neuropsychiatric Association, Oct. 21, 2017.

Soo Rim Noh et al., "Understanding eye movements during facial emotion recognition in schizophrenia", KNPA Annual Meeting 2018, Apr. 20, 2018.

Kim, Taehyun, "Eye Movements in Schizophrenia During Facial Emotion Recognition Using Hidden Markov Models", Engineering in Medicine and Biology Society, Jul. 18, 2018.

Soo Rim Noh et al., "Eye movements in schizophrenia during facial emotion recognition using Hidden Markov Models", KNPA Regional Meeting 2018, Oct. 21, 2018.

Yohan Kim, "Eye Mouvements in Schizophrenia during Facial Emotion Recognition", 2018 Annual Conference of Korean Psychological Association, Aug. 17, 2018.

* cited by examiner

TRAINING TEMPLATE CONSTRUCTION APPARATUS FOR FACIAL EXPRESSION RECOGNITION AND METHOD THEREOF

CROSS-REFERENCE TO RELATED APPLICATION

This application claims priority to and the benefit of Korean Patent Application No. 10-2018-0115261 filed in the Korean Intellectual Property Office on Sep. 27, 2018, the entire contents of which are incorporated herein by reference.

BACKGROUND OF THE INVENTION

(a) Field of the Invention

The present invention provides a training template construction apparatus for facial expression recognition and a method thereof.

(b) Description of the Related Art

Schizophrenia is mental disorder that causes clinical abnormal symptoms in a wide range throughout various aspects of personality, such as thinking, emotion, perception, and behavior. In general, schizophrenia is a disorder including positive symptoms such as auditory hallucination, delusion, unclear or confused thinking, and a strange and confused behavior and negative symptoms such as reduced social engagement, mutism, emotional flattening, anhedonia, a lack of motivation, physical handicap, and suspension of thinking.

Negative symptoms of such schizophrenia patients related to the social function and sociality such as emotional flattening and cognitive disorder are likely to become serious over time even if positive symptoms such as hallucination, delusion, and illogical thinking attenuate or improve.

The negative symptoms degrade a social function and, thus, schizophrenia patients frequently have a difficulty in leading a normal social life.

Particularly, schizophrenia patients have insufficient ability to recognize other emotion and to feel empathy and one of functions that draw an attention with regard to the ability to feel empathy in a field of such social recognition is an emotion recognition function.

Thereamong, ability to accurately infer an emotional state of others through their facial expression and to determine facial expression appropriate to an emotional state is one of important nonverbal methods for making the human social life smooth.

Accordingly, there is a need for technology for training emotion recognition ability for improving the ability to recognize and determine facial expression and emotion of schizophrenia patients to enhance sociality.

The above information disclosed in this Background section is only for enhancement of understanding of the background of the invention and therefore it may contain information that does not form the prior art that is already known in this country to a person of ordinary skill in the art.

SUMMARY OF THE INVENTION

According to an embodiment of the present invention, a training template construction apparatus for facial expression recognition may include a gaze fixation point receiving unit for receiving gaze fixation points of a user that looks a facial picture that expresses random emotion, from an eye tracking apparatus that is operatively associated with the gaze fixation point receiving unit, a gaze pattern extraction unit for extracting a gaze pattern and gaze pattern information via machine-learning of the gaze fixation points received from the gaze fixation point receiving unit, a heat map deduction unit for deducing a heat map using the gaze pattern and the gaze pattern information that are extracted by the gaze pattern extraction unit, a difference heat map deduction unit for deducing a difference value between the heat map deduced from the heat map deduction unit and a heat map of a reference group based on pre-stored facial pictures that express the same emotion and for deducing a difference heat map to which the difference value is applied, and a controller for analyzing the gaze pattern and the difference heat map to generate a training template of a sequence, a time, and a path for user gaze treatment.

The gaze pattern extraction unit may extract the gaze pattern and gaze pattern information including an average gaze fixing time when a gaze stays at a facial expression region in the facial picture and a path along which a gaze is moved, from the gaze fixation points.

The heat map deduction unit may apply a weight value to the gaze pattern and gaze pattern information to deduce a heat map indicating distribution of different colors in the facial picture depending on a degree of a gaze ratio through the gaze pattern to which the weight value is applied.

The difference heat map deduction unit may analyze the deduced difference value, may indicate a region on which a gaze concentrates in the user gaze pattern compared with a gaze pattern of a reference group, in first color, and may indicate a region on which a gaze concentrates compared with the user gaze pattern in the gaze pattern of the reference group, in second color that is complementary color of the first color.

The controller may generate a training template including a time when a gaze is fixed and a path along which a gaze is moved to allow the gaze of the user to concentrate on a region indicated in the second color for a predetermined time or greater.

The controller may set a time when a gaze is fixed and a path along which a gaze is moved to dispose the region around the mouth at a rear portion of the path along which the gaze is moved or to pass or avoid the region around the mouth when a user gaze pattern is locally indicated in the region around the mouth of a facial picture indicating specific emotion.

According to another exemplary embodiment of the present invention, a method of a training template construction apparatus for facial expression recognition may include receiving gaze fixation points of a user that looks a facial picture that expresses random emotion, from an operatively associated eye tracking apparatus, extracting a gaze pattern and gaze pattern information via machine-learning of the gaze fixation points, deducing a heat map using the gaze pattern and the gaze pattern information, deducing a difference value between the heat map and a heat map of a reference group based on pre-stored facial pictures that express the same emotion and deducing a difference heat map to which the difference value is applied, and analyzing the gaze pattern and the difference heat map to generate a training template of a sequence, a time, and a path for user gaze treatment.

According to another exemplary embodiment of the present invention, a computer readable recording medium may have recorded thereon a program for executing a method of providing a training template generated through a training template construction apparatus, wherein the program may execute a function of providing a facial picture that expresses random emotion, a function of receiving a word indicating emotion of the facial picture from a user, a function of determining whether the received word and the emotion of the facial picture correspond to each other, and a function of indicating a specific region of the facial picture and directing a gaze at the specific region of the facial picture for n seconds, or providing gaze movement path points based on the specific region of the facial picture, and directing a gaze for m seconds for each gaze movement path when the received word and the emotion of the facial picture do not correspond to each other as a determination result.

According to an exemplary embodiment of the present invention, symptoms of a schizophrenia patient may be improved and disease progression may be alleviated through a nonpharmacologic training process, a laymen that is not an expert may be easily lead a training process or may participate in the training process to achieve easy access to training, and a limitation of a place and a time may be minimized.

According to an exemplary embodiment of the present invention, a patient with developmental disability with low recognition of emotion of others, any patient with dementia, Parkinsonism, or the like, or ordinary people as well as schizophrenia patients may improve emotion recognition and empathy of others to improve sociality through training for sociality improvement.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE EMBODIMENTS

Figure 1:
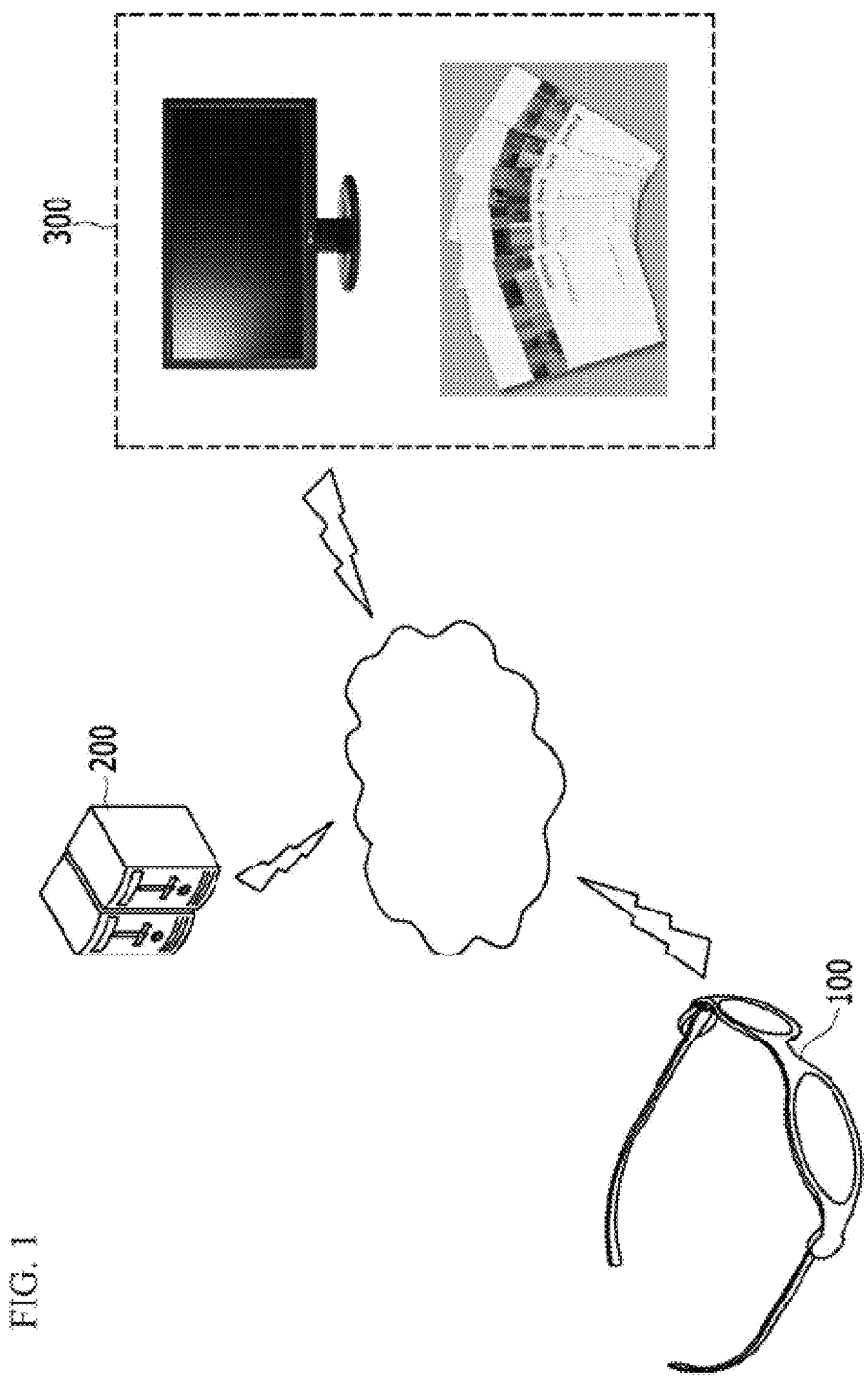
FIG. 1 is a schematic diagram showing a network including a training template construction apparatus according to an exemplary embodiment of the present invention.

Exemplary embodiments of the present invention are described in detail so as for those of ordinary skill in the art to easily implement with reference to the accompanying drawings. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification. In addition, certain detailed explanations of well known art are omitted.

In the specification, when a certain part "includes" a certain component, this indicates that the part may further include another component instead of excluding another component unless there is no different disclosure.

FIG. 1 is a schematic diagram showing a network including a training template construction apparatus according to an exemplary embodiment of the present invention.

As shown in FIG. 1, an eye tracking apparatus 100, a training template construction apparatus 200, and a training template providing apparatus 300 may be connected with each other through a communication network to transmit and receive data to and from each other.

Here, the communication network may include any type communication network for transmitting data such as a wired communication network, a short or long distance wireless communication network, and a mixed network thereof.

First, the eye tracking apparatus 100 may refer to an apparatus for recognizing a user body and extracting, tracking, and recording a user gaze. Accordingly, the eye tracking apparatus 100 may extract a point on which the user gaze settles from an environment at which the user looks.

FIG. 1 illustrates the case in which the eye tracking apparatus 100 is a goggle type apparatus that contacts directly a part of the user body but the present invention is not limited thereto. In the present invention, the eye tracking apparatus 100 may include all non-contact type apparatuses for capturing a gaze video image of the user and analyzing the gaze video image to extract gaze fixation points as well as the contact type apparatus.

The eye tracking apparatus 100 may extract gaze fixation points of the user over time and may transmit the gaze fixation points to the training template construction apparatus 200 or the training template providing apparatus 300.

Then, the training template construction apparatus 200 may deduce a gaze pattern based on a reference group and the gaze fixation point of the user and may generate a heat map and a difference heat map through the deduced gaze pattern.

The training template providing apparatus 300 may generate a facial expression recognition training template of the user based on the difference heat map.

In this case, the user is the human who has a difficulty in determining emotion from the human facial expression or has inaccuracy and may include a schizophrenia patient, a patient with developmental disability, any patent corresponding thereto, ordinary people, and so on.

Then, the training template providing apparatus 300 may refer to an apparatus for providing a training template generated by the training template construction apparatus 200 to the user. The training template providing apparatus 300 may include various apparatuses based on a type of the generated training template.

For example, when the training template is manufactured in software such as a program, an application (APP), or an electronic book, the training template providing apparatus 300 may be a readable recording medium with a corresponding program stored therein and may include a smart terminal, a computer, a personal digital assistant (PDA), a tablet PC, a smart device, or the like.

As such, the training template providing apparatus 300 may include any apparatus for providing the generated training template to the user.

Hereinafter, a training template construction method for recognizing the human facial expression according to an exemplary embodiment of the present invention is described in detail with reference to FIGS. 2 to 11.

Figure 2:
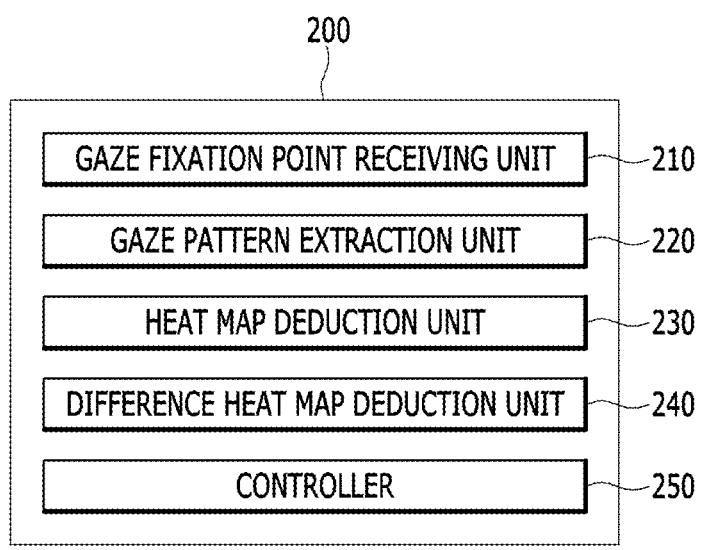
FIG. 2 is a schematic diagram of a training template construction apparatus according to an exemplary embodiment of the present invention.

FIG. 2 is a schematic diagram of a training template construction apparatus according to an exemplary embodiment of the present invention.

As shown in FIG. 2, the training template construction apparatus 200 는 a gaze fixation point receiving unit 210, a gaze pattern extraction unit 220, a heat map deduction unit 230, a difference heat map deduction unit 240, and a controller 250.

First, the gaze fixation point receiving unit 210 may receive gaze fixation points deduced from eye movement of the user from the eye tracking apparatus 100 that is operatively associated with the gaze fixation point receiving unit 210. In this case, the user currently looks at a facial picture of the human that expresses specific emotion and, in this case, the eye tracking apparatus 100 may track the user gaze in a contact or non-contact manner.

The gaze fixation point receiving unit 210 may receive gaze fixation points in a time sequence.

Then, the gaze pattern extraction unit 220 may machine-learn the gaze fixation points received from the gaze fixation point receiving unit 210 to extract a gaze pattern of the user and gaze pattern information.

The gaze pattern extraction unit 220 may analyze a plurality of gaze fixation points to extract a gaze pattern through big data-based machine learning. In this case, the big data-based machine learning may include a hidden Markov model (HMM) but is not limited thereto.

Then, the heat map deduction unit 230 may extract a heat map using the gaze pattern and the gaze patter information that are extracted by the gaze pattern extraction unit 220.

Here, the heat map is a word obtained by combination of a heat and a map and refers to output of various information items to be expressed in color on a predetermined image in the form of heat distribution type visual graphics.

Accordingly, the heat map deduction unit 230 may generate a heat map to intuitively recognize a region on which a user gaze concentrates in the facial picture that expresses emotion using the user gaze pattern and the gaze pattern information.

Then, the difference heat map deduction unit 240 may deduce a difference value between the heat map deduced from the heat map deduction unit 230 and a heat map of a reference group based on pre-stored facial pictures that express the same emotion.

The difference heat map deduction unit 240 may apply the deduced difference value of the user and the reference group to deduce the difference heat map.

Here, the reference group refers to a group of ordinary people who do not have a difficulty in determining emotion from a facial picture.

A database (not shown) that is operatively associated with the difference heat map deduction unit 240 may store the gaze pattern and the heat map that are extracted through machine learning of the reference group.

The difference heat map deduction unit 240 generates the difference value between the heat maps of the reference group and the user as a reference and, thus, may express a region on which a gaze in the reference group concentrates and the region on which the user gaze concentrates in different colors on each facial picture.

Then, the controller 250 may analyze the gaze pattern and the difference heat map that are deduced by the gaze pattern extraction unit 220 to generate a training template of a sequence, a time, and a path for user gaze treatment.

In this case, the controller 250 may generate a further intensified training template stepwise during proposal of a gaze treatment method.

The controller 250 may convert the size, shape, construction, and so on of the training template that is generated to correspond to a type of the training template providing apparatus 300 that is operatively associated with the controller 250.

For example, the controller 250 may generate the training template in the form of data and may convert the data in the form of a specific file. In detail, the controller 250 may convert the data in the printable form such as a book or a pamphlet or a three-dimensional (3D) shape. The controller 250 may generate the training template to be provided as a feedback according to a user input using a smart device or the like.

The training template construction apparatus 200 may be configured in the form of a server, a terminal, or a combination thereof.

The terminal refers to any device that includes a memory and a processor to have operation processing capability. For example, the terminal may include a personal computer, a handheld computer, a personal digital assistant (PDA), a mobile phone, a smart device, a tablet PC, or the like.

The server may include a memory for storing a plurality of modules, a processor that is connected with the memory, reacts with the plurality of modules, and processes service information provided to the terminal or action information for controlling the service information, a communication device, and a user interface (UI) display device.

The memory may be a device for storing information and may include various types of memories such as a high-speed random access memory, a magnetic disk storage device, a flash memory device, or a non-volatile memory including other non-volatile solid-state memory devices or the like.

The communication device may transmit and receive the service information or the action information to or from the terminal in real time.

The UI display device may output the service information or the action information of a system in real time. The UI display device may an independent device that directly or indirectly outputs or displays a user interface (UI) or may be a part of the device.

Hereinafter, a procedure of constructing a training template for a schizophrenia patient as a target is described but, as necessary, the procedure may be applicable to ordinary people or patents with other diseases, which have a difficulty in recognizing the human emotional facial expression.

Figure 3:
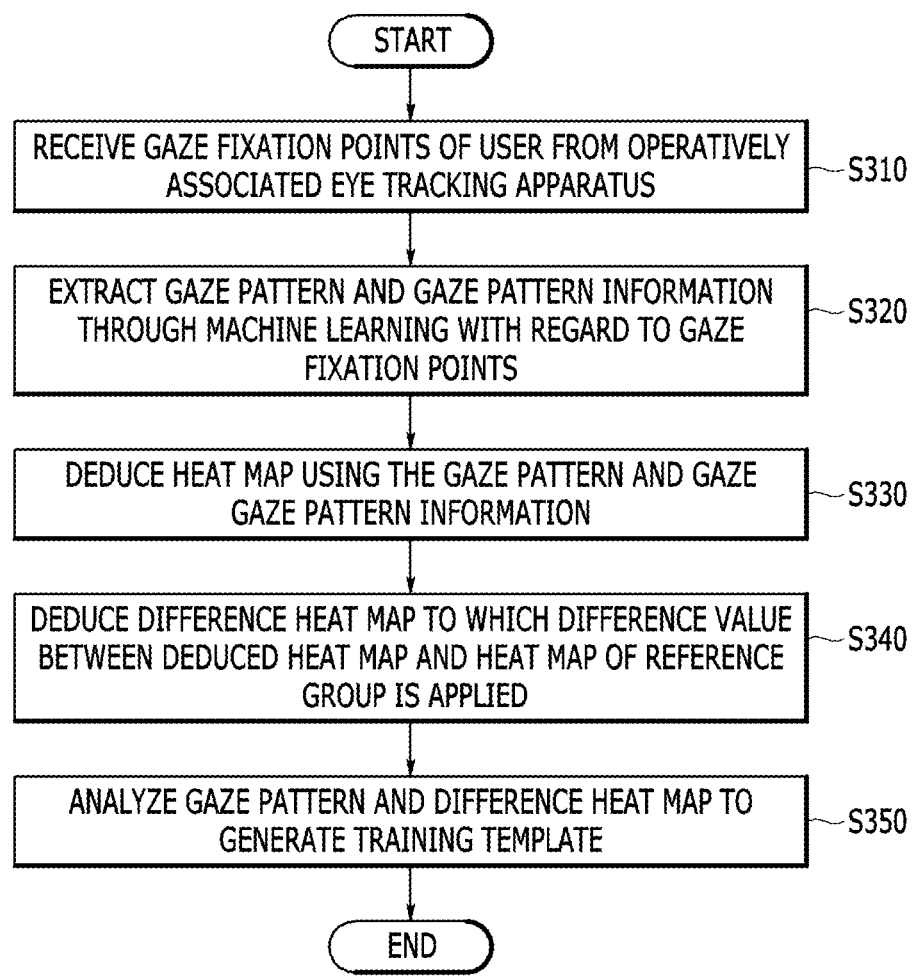
FIG. 3 is a flowchart of a construction method of a training template construction apparatus according to an exemplary embodiment of the present invention.

FIG. 3 is a flowchart of a construction method of a training template construction apparatus according to an exemplary embodiment of the present invention.

The training template construction apparatus 200 according to an exemplary embodiment of the present invention may receive gaze fixation points of the user who looks at a facial picture that expresses emotion, from the eye tracking apparatus 100 that is operatively associated with the training template construction apparatus 200 (S310).

Here, the emotion of the facial picture may include anger, sadness, fear, disgust, happiness, neutral emotion, or the like and may further include various emotions.

Then, the training template construction apparatus 200 may extract a gaze pattern and gaze pattern information through machine learning with regard to gaze fixation points (S320).

The training template construction apparatus 200 may extract the gaze pattern from the gaze fixation points using a hidden Markov model (HMM).

The training template construction apparatus 200 may analyze the gaze fixation points in a time sequence to extract a gaze path and may extract the gaze pattern information including a region in which the gaze fixation points overlap with each other, a time when a gaze stays at one point, or the like.

As such, the training template construction apparatus 200 may extract three gaze patterns using the hidden Markov model (HMM).

As such, the analysis result of the gaze pattern extracted by the training template construction apparatus 200 is shown in FIGS. 4 to 7.

Figure 4:
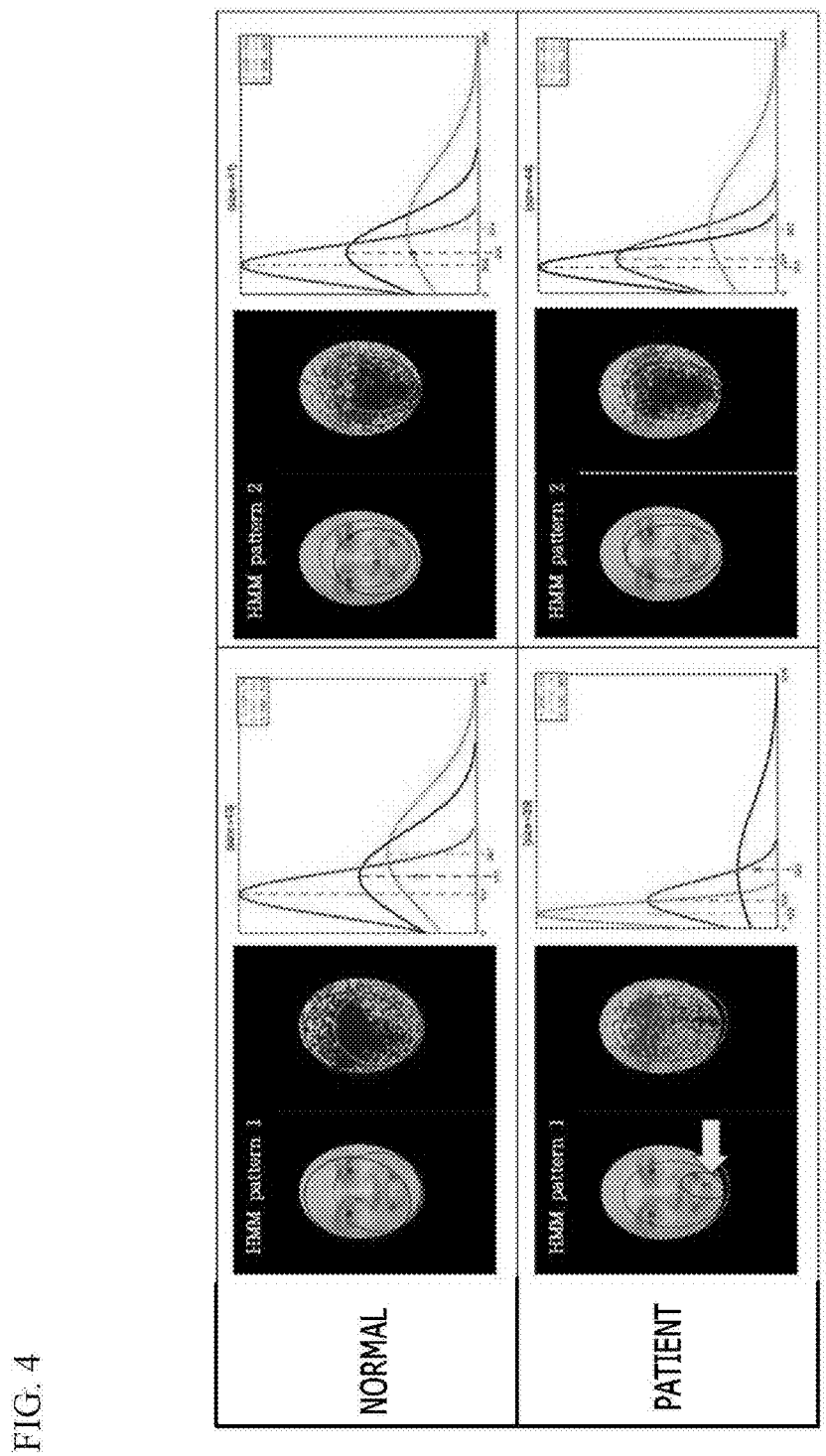
FIG. 4 is a diagram showing examples of gaze patterns of a normal group and a patient group who recognize a facial picture indicating anger according to an exemplary embodiment of the present invention.
Figure 5:
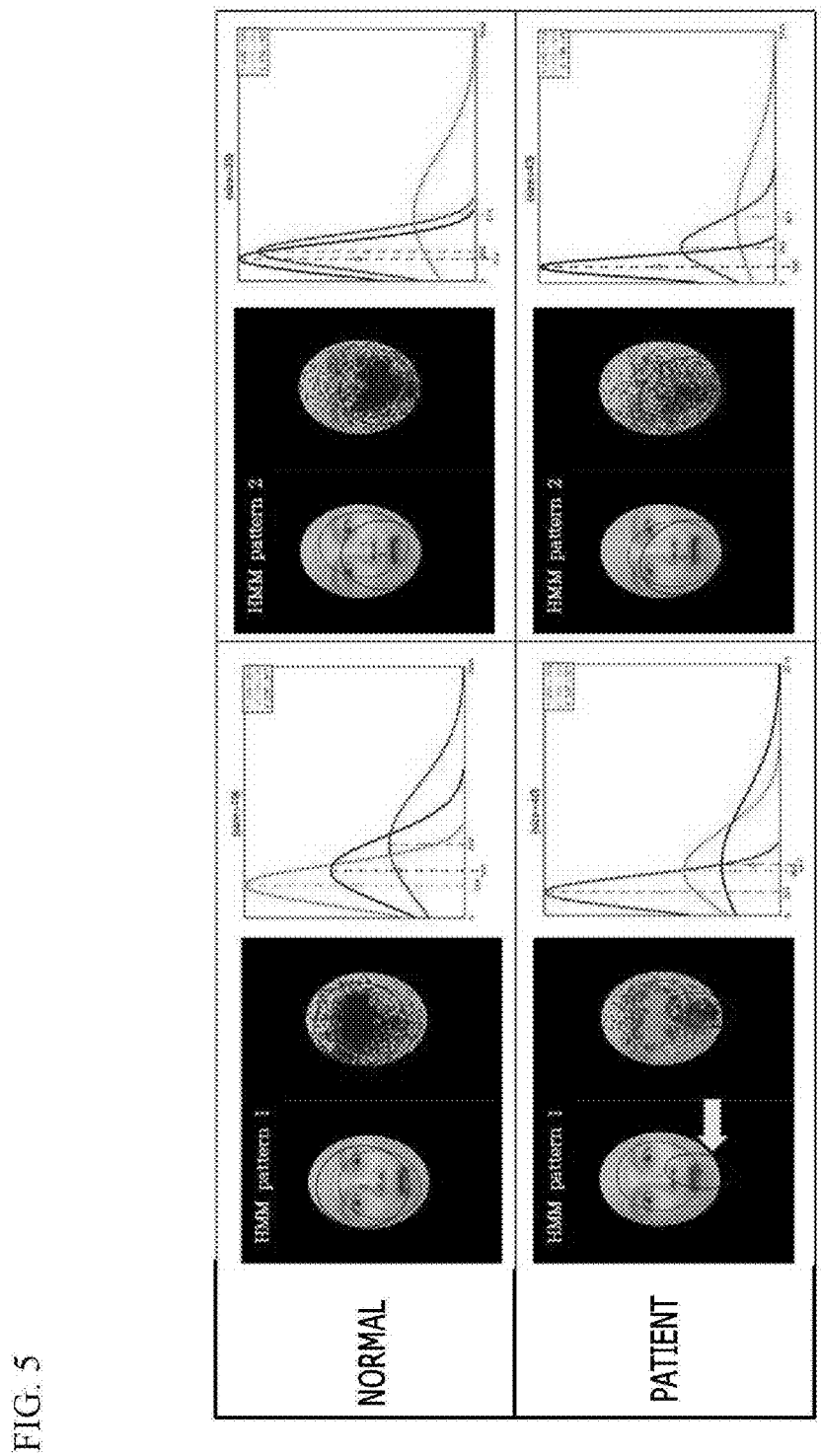
FIG. 5 is a diagram showing examples of gaze patterns of a normal group and a patient group who recognize a facial picture indicating fear according to an exemplary embodiment of the present invention.

FIG. 4 is a diagram showing examples of gaze patterns of a normal group and a patient group who recognize a facial picture indicating anger according to an exemplary embodiment of the present invention. FIG. 5 is a diagram showing examples of gaze patterns of a normal group and a patient group who recognize a facial picture indicating fear according to an exemplary embodiment of the present invention.

Figure 6:
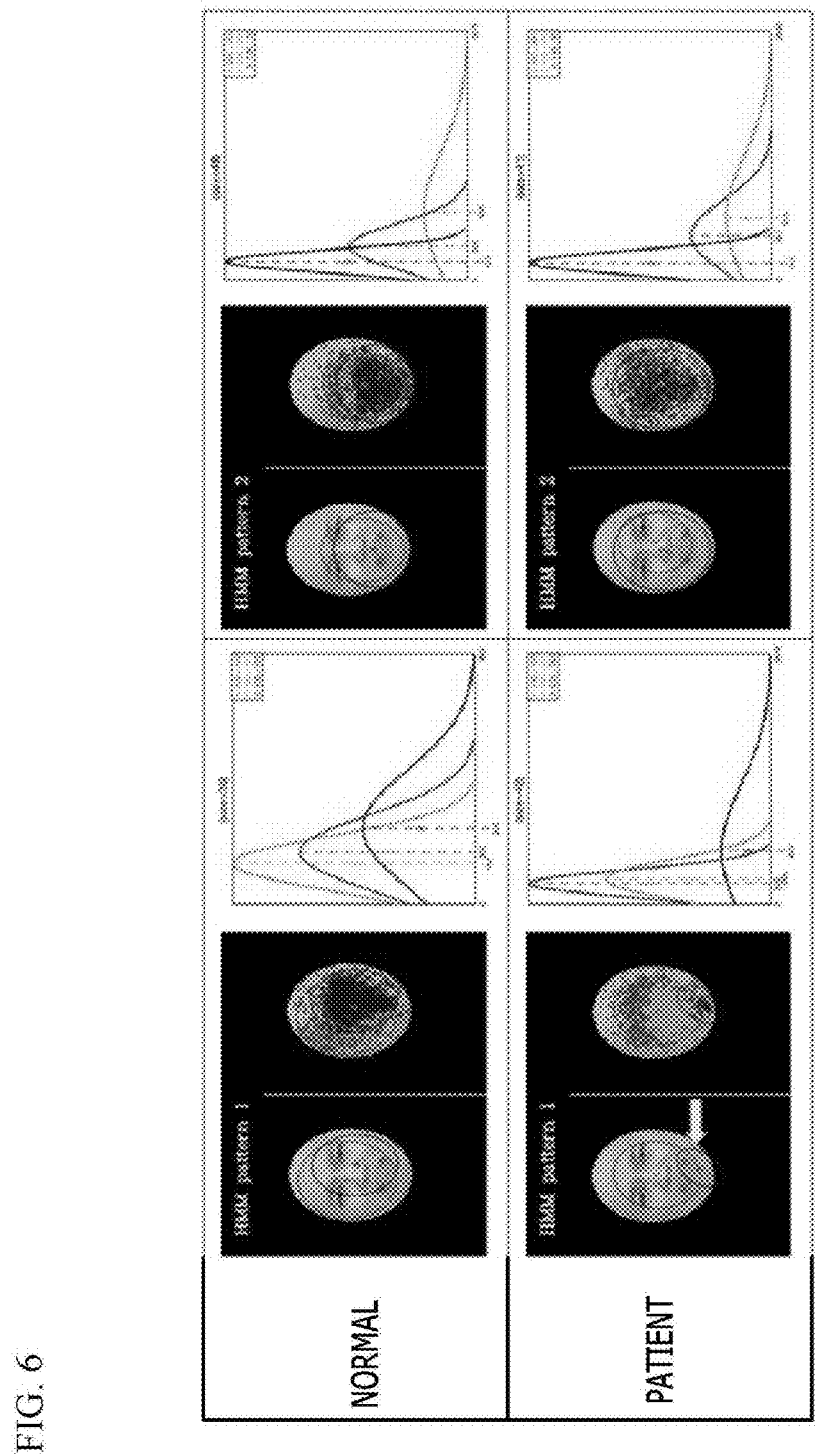
FIG. 6 is a diagram showing examples of gaze patterns of a normal group and a patient group who recognize a facial picture indicating disgust according to an exemplary embodiment of the present invention.
Figure 7:
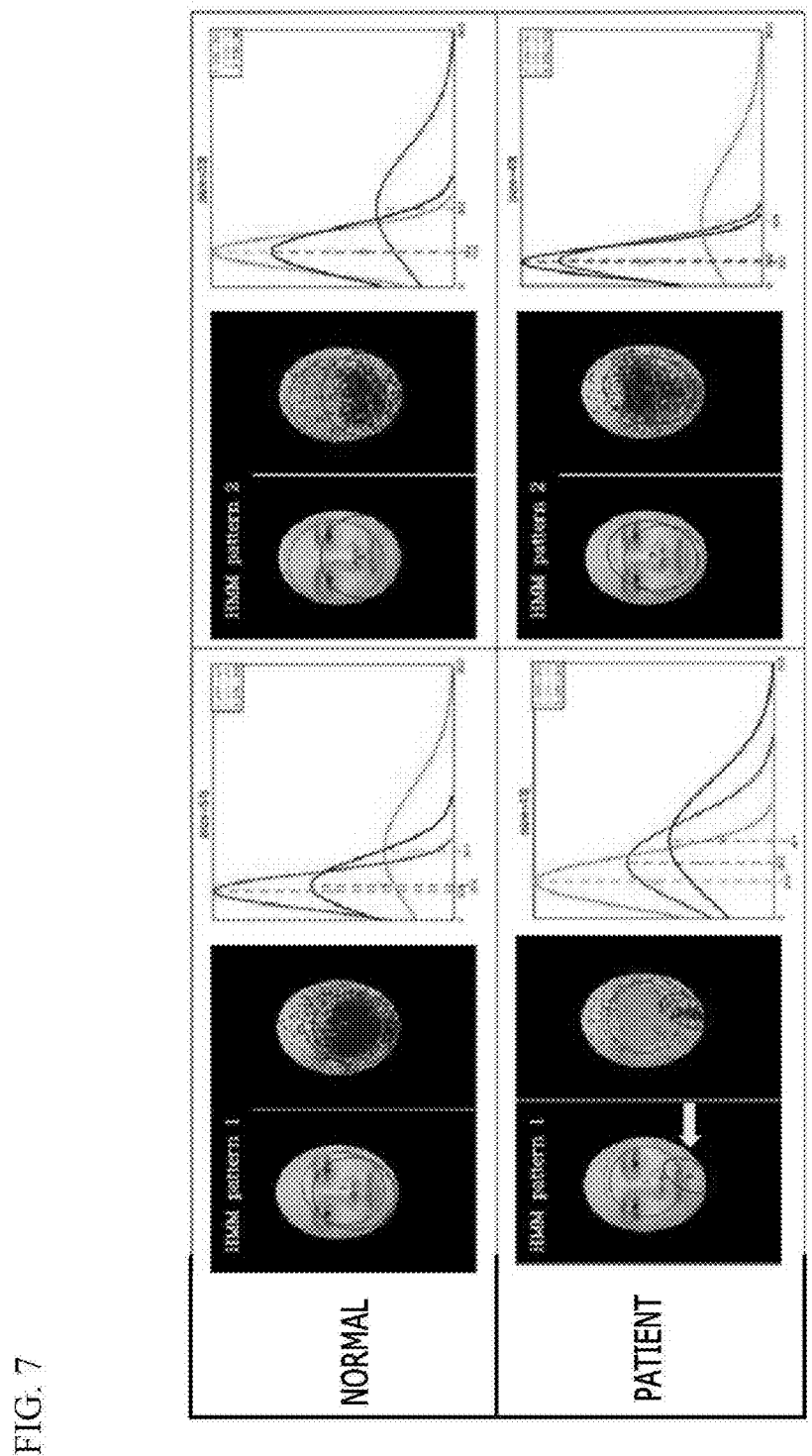
FIG. 7 is a diagram showing examples of gaze patterns of a normal group and a patient group who recognize a neutral facial picture according to an exemplary embodiment of the present invention.

FIG. 6 is a diagram showing examples of gaze patterns of a normal group and a patient group who recognize a facial picture indicating disgust according to an exemplary embodiment of the present invention. FIG. 7 is a diagram showing examples of gaze patterns of a normal group and a patient group who recognize a neutral facial picture according to an exemplary embodiment of the present invention.

FIGS. 4 to 7 are diagrams showing examples of pattern 1 (HMM pattern 1) and pattern 2 (HMM pattern 2) that are extracted through a hidden Markov model (HMM) corresponding to each of a reference group (normal) and a user (patient) with regard to facial pictures that express respective different emotions.

Here, pattern 1 (HMM pattern 1) and pattern 2 (HMM pattern 2) of the reference group correspond to the cases that are identified depending on a pattern aspect irrespective of whether emotion is accurately determined in a facial picture. In detail, pattern 1 in a user (patient) group may be classified as a pattern with a low emotion determination ratio of a facial picture in a schizophrenia patient group and pattern 2 may be classified as a pattern with a satisfactory emotion determination ratio of a facial picture in a schizophrenia patient group.

In addition, three areas of interest (AOIs) are extracted and indicated in each of pattern 1 and pattern 2 to verify a difference between the reference group and the user.

First, as seen from FIG. 4, in pattern 1 and pattern 2 of the reference group (normal) and pattern 2 of the user (patient), three gaze patterns (AOI: a blue circle, a red circle, and a green circle) commonly and similarly indicate a facial expression region and, on the other hand, in pattern 1 of the user (patient), a blue circle is locally indicated around the mouth.

Similarly, referring to FIGS. 5 to 7, commonly, the reference group (normal) is most largely different from the user (patient) in that a blue circle of pattern 1 of the user (patient) is locally indicated around the mouth.

Accordingly, it may be seen that a schizophrenia patient with a low emotion determination ratio of a facial picture has a gaze pattern staying around the mouth and, thus, is not capable of recognizing an overall facial picture and is not capable of recognizing emotion.

Then, the training template construction apparatus 200 may deduce a heat map using the gaze pattern and the gaze pattern information (S330).

The training template construction apparatus 200 may apply a weight value to the user gaze pattern and the gaze pattern information to highlight the feature of the user gaze pattern.

The training template construction apparatus 200 may generate distribution with different colors depending on a degree of a gaze ratio to generate a heat map through the gaze pattern to which the weight value is applied.

Figure 8:
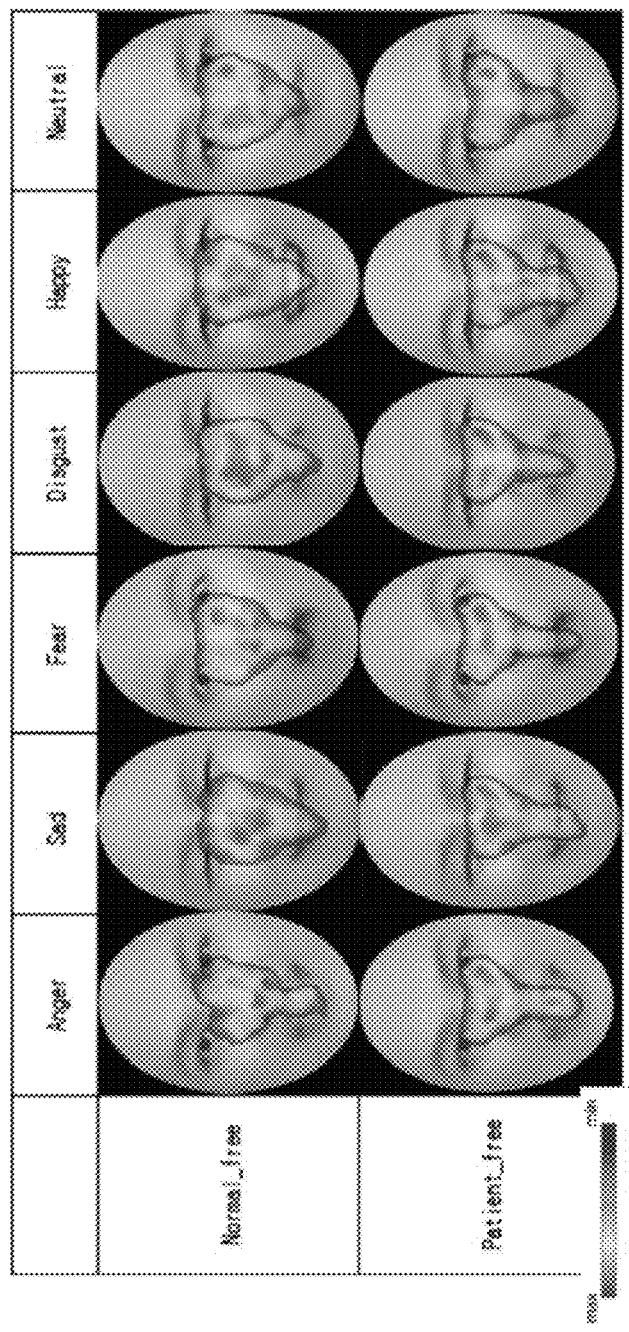
FIG. 8 is a diagram showing examples of heat maps of a normal group and a patient group according to an exemplary embodiment of the present invention.

FIG. 8 is a diagram showing examples of heat maps of a normal group and a patient group according to an exemplary embodiment of the present invention.

Referring to FIG. 8, in a heat map of each of a reference group (Normal_free) and a user (Patient_free) in facial pictures indicating six emotions, as red deepens, a gaze ratio is increased and, as blue deepens, a gaze ratio is reduced.

As seen from FIG. 8, the heat map of the reference group has different gaze patterns based on respective emotions for each emotion. This is because a gaze treatment method is changed based on each emotion since facial regions that are changed and highlighted depending on various emotions are different.

However, a heat map of the user may be indicated with almost the same gaze pattern in various emotion pictures.

With regard to the heat map of the user, a gaze concentrates on a T-shape region of the eyes, nose, and mouth and, thus, there is a limit in recognizing sufficient information to recognize various emotions expressed on a face of a counterpart.

Then, the training template construction apparatus 200 may deduce a difference heat map to which the difference value between the deduced heat map and the heat map of the reference group is applied (S340).

Figure 9:
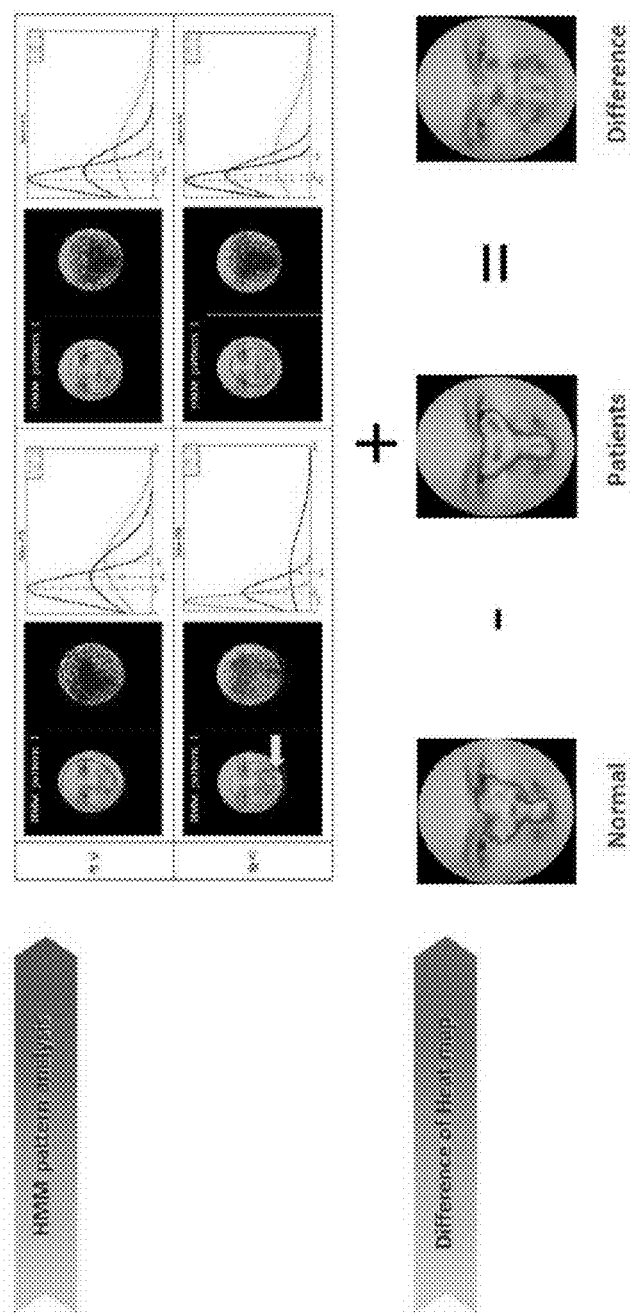
FIG. 9 is a diagram showing an example of a procedure of generating a difference heat map according to an exemplary embodiment of the present invention.

FIG. 9 is a diagram showing an example of a procedure of generating a difference heat map according to an exemplary embodiment of the present invention.

As shown in FIG. 9, the training template construction apparatus 200 may deduce a new difference heat map to which a difference between a heat map of a reference group and a heat map of a user is applied, based on the heat map deduced through a gaze pattern extracted through a HMM pattern algorithm.

The training template construction apparatus 200 may indicate a region on which a gaze concentrates in a user gaze pattern compared with a gaze pattern of a reference group, in first color, and may indicate a region on which a gaze concentrates compared with the user gaze pattern in the gaze pattern of the reference group, in second color that is complementary color of the first color.

For example, as shown in FIG. 9, the training template construction apparatus 200 may indicate blue as the first color and red as the second color and, thus, may visually generate a difference heat map to intuitively and easily recognize a portion with a high ratio in the gaze pattern between the reference group and the user, through complementary color.

Figure 10:
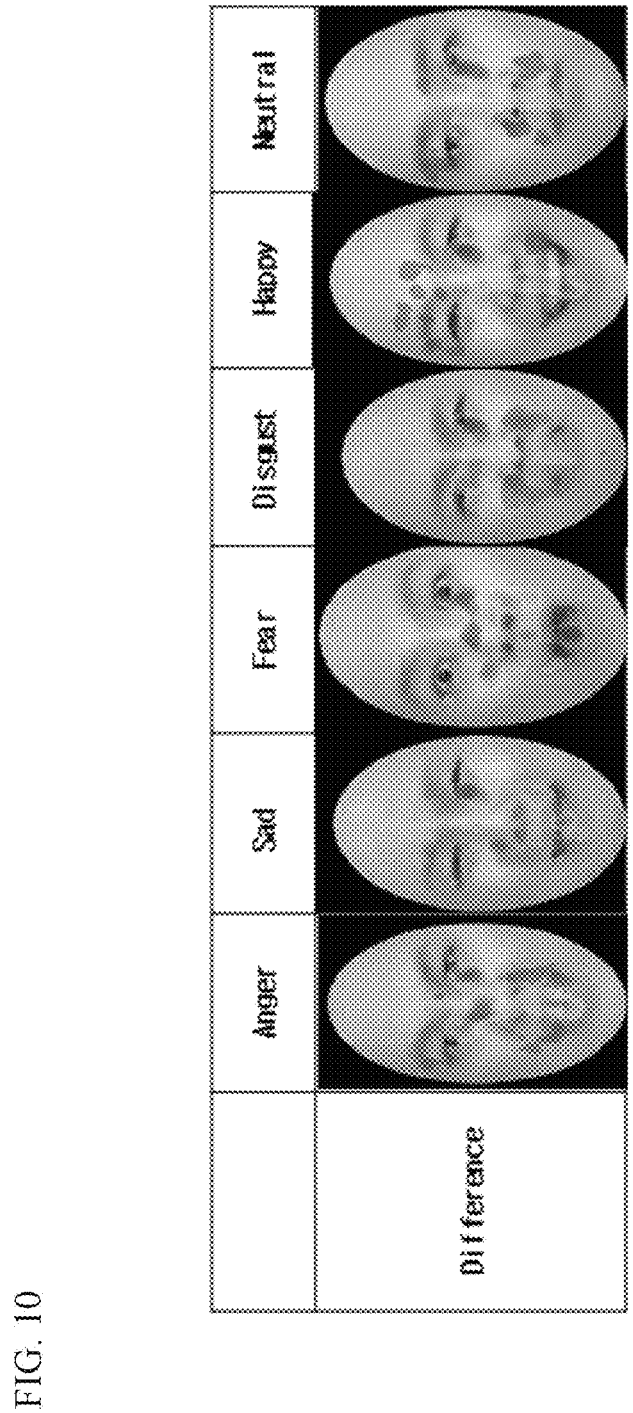
FIG. 10 is a diagram showing an example of a difference heat map indicated for each emotion according to an exemplary embodiment of the present invention.

FIG. 10 is a diagram showing an example of a difference heat map indicated for each emotion according to an exemplary embodiment of the present invention.

FIG. 10 shows a difference heat map about anger, sadness, fear, disgust, happiness, and neutral emotion.

As shown in FIG. 10, a region indicated with green and blue may be indicated as a portion on which a user gaze concentrates with a high ratio and red and orange regions other than a T-shape region may be indicated as a portion on which a gaze of a reference group concentrates with a higher ratio.

In other words, the T-shape region around the eyes, nose, and mouth may be a portion on which a user gaze concentrates with a high ratio and a region such as mouth wrinkle of opposite sides, middle of the forehead, and a left eye rim may be a portion on which a gaze of the reference group concentrates with a higher ratio.

The training template construction apparatus 200 may generate a training template based on a difference of gaze difference between the reference group and the user (S350).

The training template construction apparatus 200 may generate a training template for each emotion using the constructed difference heat map and the gaze pattern extracted in operation in S320.

Figure 11:
FIG. 11 is a diagram showing an example of a training template according to an exemplary embodiment of the present invention.

FIG. 11 is a diagram showing an example of a training template according to an exemplary embodiment of the present invention.

In FIG. 11, a reference group (Normal) and a user (Patients) use two patterns and different difference heat maps for the respective patterns.

With regard to pattern 1 of the user (Patients) with the most different pattern in FIG. 11, a blue circle limited around the mouth of a facial picture is especially indicated in the emotion of anger, fear, disgust, and neutral emotion.

The blue circle refers to an area of interest (AOI) of a user, which is deduced from the pattern of the HMM. When the area of interest (AOI) of a schizophrenia patient corresponds to a blue circle, the blue circle is barely moved or transitioned to a red or green circle that is another area of interest (AOI) and, thus, a gaze treatment region is narrowed to lower a facial expression recognition ratio of the schizophrenia patient.

Accordingly, when the user gaze pattern concentrates on a region around the mouth in a facial picture indicating specific emotion of anger, fear, disgust, and neutral emotion, the training template providing apparatus 300 may generate a training template to minimize a user gaze in the region around the mouth.

In more detail, the training template providing apparatus 300 may set a time when a gaze is fixed and a path along which a gaze is moved to dispose the region around the mouth at a rear portion of the path along which the gaze is moved or to pass or avoid the region around the mouth.

In addition, the training template providing apparatus 300 may generate the training template to allow a gaze to concentrate on a region on which the gaze is concentrated with a higher ratio in the reference group indicated in the second color.

For example, the training template providing apparatus 300 may generate the training template that indicates the region indicated in the second color to order the user to observe the corresponding region for a predetermined time or greater.

As such, the training template providing apparatus 300 may refine instructions for each predetermined step and may generate various training templates to guide the user gaze to concentrate on a region on which the gaze concentrates with a higher ratio in the reference group compared with the user for each emotion expressed in the facial picture and to prevent the user gaze from staying in the region around the mouth.

Hereinafter, a procedure of providing a training template through a training template providing apparatus is described in detail with reference to FIGS. 12 and 13.

Figure 12:
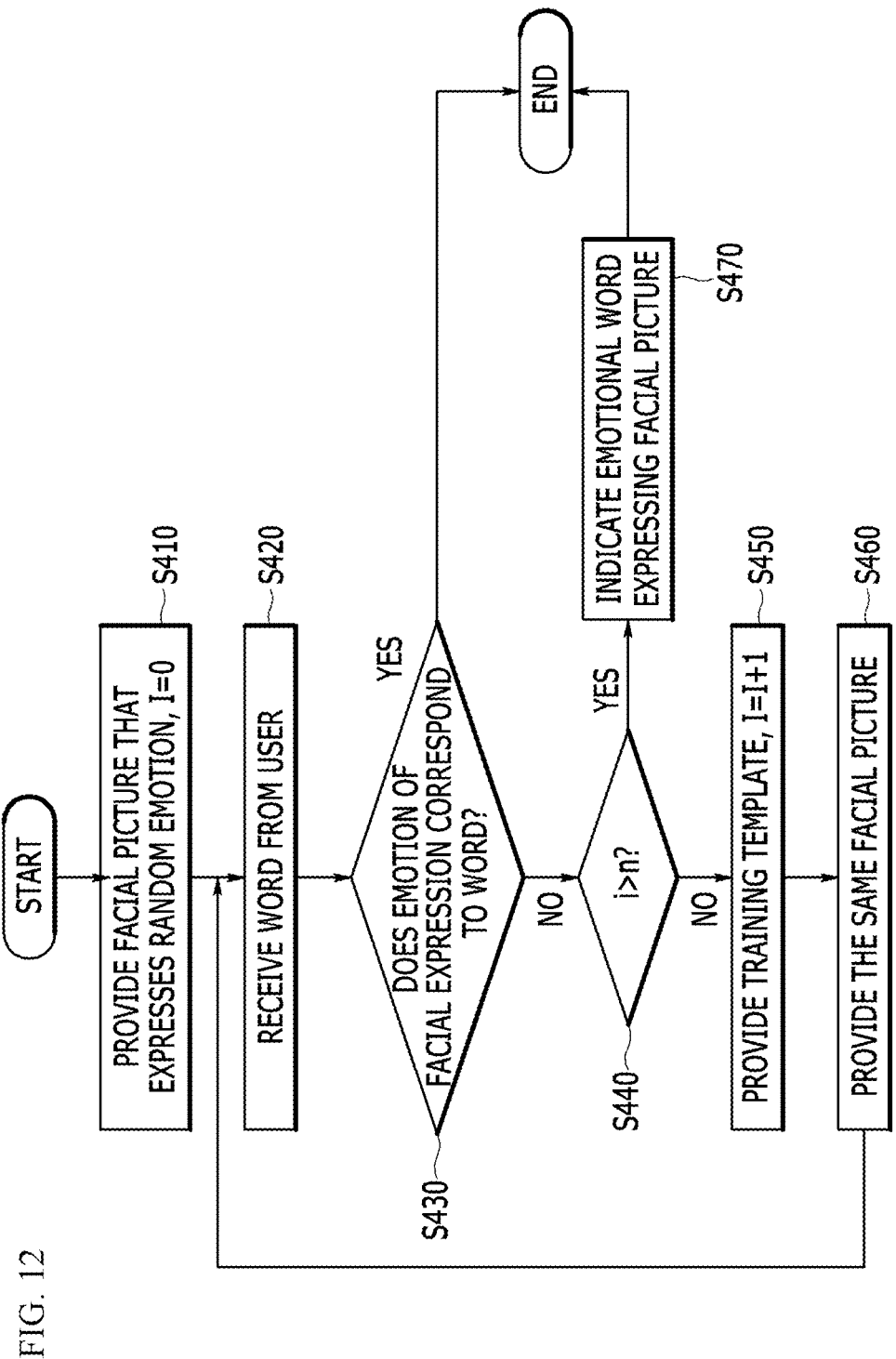
FIG. 12 is a flowchart of a method of providing a training template according to an exemplary embodiment of the present invention.

FIG. 12 is a flowchart of a method of providing a training template according to an exemplary embodiment of the present invention. FIG. 13 A, FIG. 13B and FIG. 13C are a diagram showing an example of a provided training template according to an exemplary embodiment of the present invention.

The training template providing apparatus 300 may provide a facial picture that expresses random emotion (S410). The training template providing apparatus 300 may set an initial value 'i' to 0 while providing a facial picture that first expresses emotion.

In this case, the training template providing apparatus 300 may randomly select and provide a facial picture among facial pictures grouped with each emotion in a separate database and a facial picture that expresses random emotion is not limited to specific gender or age.

Then, the training template providing apparatus 300 may receive a word indicating emotion of a facial picture from the user (S420).

In this case, the training template providing apparatus 300 may receive the word directly from the user or may provide words indicating several different emotions and, then, may receive information on a specific word according to user selection among the provided words.

Then, the training template providing apparatus 300 may determine whether the received word corresponds to the emotion of the facial picture (S430).

In this case, as the determination result, when the received word expresses the emotion of the facial picture, the procedure may be terminated or the facial picture that expresses random emotion may be provided.

As the determination result, when the received word does not express the emotion of the facial picture, the training template providing apparatus 300 may compare a value 'i' and a predetermined value 'n' (S440). Here, 'n' may be a threshold value as a natural number and may be easily changed and designed by the user.

When a number of times do not correspond to a predetermined number, the training template providing apparatus 300 may provide a training template (S450).

The training template providing apparatus 300 may select and provide different training template depending on 'i' among at least one training template that is operatively stored for each facial picture.

Here, the training template may be generated based on the difference heat map to which the gaze pattern of the schizophrenia patient group and a difference value between a heat map of the schizophrenia patient group and a heat map of the reference group are applied.

In the training template, a region on which a gaze concentrates in the gaze pattern of the reference group compared with the gaze pattern of the schizophrenia patient group may be indicated as a specific region in a facial picture, based on the difference heat map. In addition, the training template may include information directing a gaze at a specific region of a facial picture for n seconds, or providing gaze movement path points based on the specific region of the facial picture, and directing a gaze for m seconds for each gaze movement path.

Here, setting of n seconds and m seconds may be easily changed by the user and, as a value 'i' is increased, n seconds and m seconds may be set to be increased to provide the same training template.

The training template providing apparatus 300 may increase the value 'i' by adding 1 while providing the training template.

Then, the training template providing apparatus 300 may provide the same facial picture (S460).

Upon determining that the user terminates learning of gaze treatment through the training template, the training template providing apparatus 300 may re-provide the facial picture provided in operation S410.

In this case, the training template providing apparatus 300 may automatically provide the same facial picture when receiving a button for proceeding to a next operation from the user or when a predetermined learning time is exceeded.

In addition, the method may return to operation S420 and operation S420 may be repeatedly performed.

Here, the training template providing apparatus 300 may provide a training template including concrete and detailed indication for each step as a value 'i' is increased.

Figure 13A:
FIG. 13A, FIG. 13B and FIG. 13C are a diagram showing an example of a provided training template according to an exemplary embodiment of the present invention.
Figure 13B:
Figure 13C:

For example, as shown in FIG. 13A, the training template providing apparatus 300 may provide a picture that expresses disgust emotion among facial pictures that express emotion that is randomly selected.

In this case, when a word that expresses emotion of a facial picture input from the user is not matched, the training template providing apparatus 300 may provide the facial picture while widening a specific region of a face and, simultaneously, may indicate a gaze at the corresponding region for 5 seconds, as shown in FIG. 13B.

Then, the training template of FIG. 13A may be re-provided and, when a word that expresses emotion of the same picture is not input, gaze treatment after a gaze at each point for a minimum of 5 seconds may be indicated while providing points as a gaze target in the facial picture and a gaze path during a gaze of each point, as shown in FIG. 13C.

As such, when a number of times that a word that expresses emotion of a facial picture input from the user is not matched is increased with respect to the same facial picture, the training template providing apparatus 300 may provide a training template indicating more detailed gaze treatment.

Then, when a value 'i' corresponds to n (which is a threshold value as a natural number) in operation S440, the training template providing apparatus 300 may not provide a training template any longer and may display an emotional word expressing a facial picture to the user (S470).

When providing a training template through feedback of the user, the training template providing apparatus 300 may verify whether the user accurately performs gaze treatment in response to the training template that is operatively associated with the eye tracking apparatus 100. When the provided training template and gaze treatment of the user do not correspond to each other, the training template providing apparatus 300 may transmit a notification message through warning horn or warning expression and may request gaze treatment corresponding to the training template again.

As such, a program for improving facial expression recognition for a schizophrenia patient who provides a training template, as a target, may be recorded in a computer readable recording medium.

The computer readable medium may include program commands, data files, or data structures alone or in combination thereof. The medium may be specially designed and configured or be known to those skilled in the field of computer software. Examples of a computer readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands. Here, the medium may be a transmission medium such as light including a carrier for transmitting a signal indicating a program command, a data structure, or the like, a metal line, or a wave guide. Examples of the program commands include a machine language code created by a compiler and a high-level language code executable by a computer using an interpreter and the like.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

100: eye tracking apparatus 200: training template construction apparatus
210: gaze fixation point receiving unit 220: gaze pattern extraction unit
230: heat map deduction unit 240: difference heat map deduction unit
250: controller 300: training template providing apparatus While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A training template construction apparatus for facial expression recognition, comprising:
 a gaze fixation point receiving unit for receiving gaze fixation points of a user that looks a facial picture that expresses random emotion, from an eye tracking apparatus that is operatively associated with the gaze fixation point receiving unit;
 a gaze pattern extraction unit for extracting a gaze pattern and gaze pattern information via machine-learning of the gaze fixation points received from the gaze fixation point receiving unit;
 a heat map deduction unit for deducing a heat map using the gaze pattern and the gaze pattern information that are extracted by the gaze pattern extraction unit;
 a difference heat map deduction unit for deducing a difference value between the heat map deduced from the heat map deduction unit and a heat map of a reference group based on pre-stored facial pictures that express the same emotion and for deducing a difference heat map to which the difference value is applied; and a controller for analyzing the gaze pattern and the difference heat map to generate a training template of a sequence, a time, and a path for user gaze treatment.

2. The training template construction apparatus of claim 1, wherein:

the gaze pattern extraction unit extracts the gaze pattern and gaze pattern information including an average gaze fixing time when a gaze stays at a facial expression region in the facial picture and a path along which a gaze is moved, from the gaze fixation points.

3. The training template construction apparatus of claim of claim 1, wherein:

the heat map deduction unit applies a weight value to the gaze pattern and gaze pattern information to deduce a heat map indicating distribution of different colors in the facial picture depending on a degree of a gaze ratio through the gaze pattern to which the weight value is applied.

4. The training template construction apparatus of claim of claim 1, wherein:

the difference heat map deduction unit analyzes the deduced difference value, indicates a region on which a gaze concentrates in the user gaze pattern compared with a gaze pattern of a reference group, in first color, and indicates a region on which a gaze concentrates compared with the user gaze pattern in the gaze pattern of the reference group, in second color that is complementary color of the first color.

5. The training template construction apparatus of claim of claim 4, wherein:

the controller generates a training template including a time when a gaze is fixed and a path along which a gaze is moved to allow the gaze of the user to concentrate on a region indicated in the second color for a predetermined time or greater.

6. The training template construction apparatus of claim of claim 1, wherein:

the controller sets a time when a gaze is fixed and a path along which a gaze is moved to dispose the region around the mouth at a rear portion of the path along which the gaze is moved or to pass or avoid the region around the mouth when a user gaze pattern is locally indicated in the region around the mouth of a facial picture indicating specific emotion.

7. A method of a training template construction apparatus for facial expression recognition, the method comprising:

receiving gaze fixation points of a user that looks a facial picture that expresses random emotion, from an operatively associated eye tracking apparatus;

extracting a gaze pattern and gaze pattern information via machine-learning of the gaze fixation points;

deducing a heat map using the gaze pattern and the gaze pattern information;

deducing a difference value between the heat map and a heat map of a reference group based on pre-stored facial pictures that express the same emotion and deducing a difference heat map to which the difference value is applied; and analyzing the gaze pattern and the difference heat map to generate a training template of a sequence, a time, and a path for user gaze treatment.

8. The method of claim 7, wherein:

the extracting of the gaze pattern and the gaze pattern information includes extracting the gaze pattern and gaze pattern information including an average gaze fixing time when a gaze stays at a facial expression region in the facial picture and a path along which a gaze is moved, from the gaze fixation points.

9. The method of claim 7, wherein:

the deducing of the heat map includes applying a weight value to the gaze pattern and gaze pattern information to deduce a heat map indicating distribution of different colors in the facial picture depending on a degree of a gaze ratio through the gaze pattern to which the weight value is applied.

10. The method of claim 7, wherein:

the deducing of the difference heat map includes analyzing the deduced difference value, indicating a region on which a gaze concentrates in the user gaze pattern compared with a gaze pattern of a reference group, in first color, and indicating a region on which a gaze concentrates compared with the user gaze pattern in the gaze pattern of the reference group, in second color that is complementary color of the first color.

11. The method of claim 10, wherein:

the generating of the training template includes generating a training template including a time when a gaze is fixed and a path along which a gaze is moved to allow the gaze of the user to concentrate on a region indicated in the second color.

12. The method of claim 7, wherein:

the generating of the training template includes setting a time when a gaze is fixed and a path along which a gaze is moved to dispose the region around the mouth at a rear portion of the path along which the gaze is moved or to pass or avoid the region around the mouth when a user gaze pattern is locally indicated in the region around the mouth of a facial picture indicating specific emotion.

13. A non-transitory computer readable recording medium having recorded thereon a program for executing a method of providing a training template generated through a training template construction apparatus, wherein the program executes a function of providing a facial picture that expresses random emotion, a function of receiving a word indicating emotion of the facial picture from a user, a function of determining whether the received word and the emotion of the facial picture correspond to each other, and a function of indicating a specific region of the facial picture and directing a gaze at the specific region of the facial picture for n seconds, or providing gaze movement path points based on the specific region of the facial picture, and directing a gaze form seconds for each gaze movement path when the received word and the emotion of the facial picture do not correspond to each other as a determination result.

14. The non-transitory computer readable recording medium of claim 13, wherein: the training template is generated based on a difference heat map to which at a gaze pattern of a schizophrenia patient group and a difference value between a heat map of the schizophrenia patient group and a heat map of the reference group are applied; and the specific region is a region on which a gaze concentrates in the gaze pattern of the reference group compared with the gaze pattern of the schizophrenia patient group.

15. The non-transitory computer readable recording medium of claim 14, wherein: the training template is generated to rapidly pass a limited region around a mouth of the facial picture or to dispose the region around the mouth at a rear portion of the path along which the gaze is moved when the facial picture is a picture indicating emotion of anger, fear, disgust, and neutral emotion.

* * * * *